US012005123B2

(12) United States Patent
Chung et al.

(10) Patent No.: US 12,005,123 B2
(45) Date of Patent: *Jun. 11, 2024

(54) CONJUGATE OF ISOTRETINOIN AND PEPTIDE

(71) Applicant: CAREGEN CO., LTD., Anyang-si (KR)

(72) Inventors: Yong Ji Chung, Seoul (KR); Eun Mi Kim, Yongin-si (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/736,261

(22) Filed: May 4, 2022

(65) Prior Publication Data

US 2022/0265840 A1    Aug. 25, 2022

Related U.S. Application Data

(62) Division of application No. 16/612,125, filed as application No. PCT/KR2018/005447 on May 11, 2018, now Pat. No. 11,351,266.

(30) Foreign Application Priority Data

May 11, 2017   (KR) .......................... 10-2017-0058866

(51) Int. Cl.
| A61K 38/10 | (2006.01) |
| A61K 8/64 | (2006.01) |
| A61K 47/64 | (2017.01) |
| A61Q 17/00 | (2006.01) |
| A61Q 19/00 | (2006.01) |
| C07K 7/08 | (2006.01) |

(52) U.S. Cl.
CPC ................ *A61K 47/64* (2017.08); *A61K 8/64* (2013.01); *A61Q 17/00* (2013.01); *A61K 2800/522* (2013.01)

(58) Field of Classification Search
CPC .......... A61K 47/64; A61K 38/10; A61K 8/64; A61K 2800/522; C07K 7/08; A61Q 17/00; A61Q 19/00
See application file for complete search history.

(56) References Cited

U.S. PATENT DOCUMENTS

| 4,371,673 | A | 2/1983 | Pitha |
| 6,441,226 | B1 | 8/2002 | Salman et al. |
| 6,669,951 | B2 | 12/2003 | Rothbard et al. |
| 7,229,961 | B2 | 6/2007 | Rothbard et al. |
| 8,003,621 | B2 | 8/2011 | Niitsu et al. |
| 8,278,264 | B2 | 10/2012 | Rothbard et al. |
| 8,623,833 | B2 | 1/2014 | Rothbard et al. |
| 8,729,010 | B2 | 5/2014 | Rothbard et al. |
| 2002/0127198 | A1 | 9/2002 | Rothbard et al. |
| 2003/0022831 | A1 | 1/2003 | Rothbard et al. |
| 2003/0161791 | A1 | 8/2003 | Bentley et al. |
| 2004/0186045 | A1 | 9/2004 | Rothbard et al. |
| 2007/0173436 | A1 | 7/2007 | Rothbard et al. |
| 2007/0213277 | A1 | 9/2007 | Rothbard et al. |
| 2007/0270472 | A1 | 11/2007 | Beumer et al. |
| 2008/0075776 | A1 | 3/2008 | Chaudhari et al. |
| 2009/0105179 | A1 | 4/2009 | Yu et al. |
| 2011/0206610 | A1 | 8/2011 | Rothbard et al. |
| 2011/0257249 | A1 | 10/2011 | Niitsu et al. |
| 2013/0096069 | A1 | 4/2013 | Rothbard et al. |
| 2013/0101662 | A1 | 4/2013 | Carreño Raïma et al. |
| 2014/0213532 | A1 | 7/2014 | Rothbard et al. |

FOREIGN PATENT DOCUMENTS

| CN | 101048375 A | 10/2007 |
| JP | 2004-530657 A | 10/2004 |
| JP | 2005-507934 A | 3/2005 |
| JP | 2008-515770 A | 5/2008 |
| JP | 2010-539245 A | 12/2010 |
| KR | 10-2002-0033751 A1 | 5/2002 |
| KR | 10-2004-0040792 A | 5/2004 |
| KR | 10-2006-0091829 A | 8/2006 |
| KR | 10-2007-0038509 A | 4/2007 |
| KR | 10-2007-0091613 A | 9/2007 |
| KR | 10-1224809 B1 | 1/2013 |
| KR | 10-2016-0121802 A | 10/2016 |

(Continued)

OTHER PUBLICATIONS

Lemos et al., "Possible oxidative effects of isotretinoin and modulatory effects of vitamins A and C in *Saccharomyces cerevisiae*," African Journal of Biotechnology, 2016, 15(6), 145-152. (Year: 2016).*

Office Action for corresponding Chinese Patent Application No. 201880031088.X issued on Oct. 13, 2022 (6 pages).

Office Action for Saudi Patent Application No. 522441026 issued on Dec. 19, 2022 (4 pages).

Lei Xing et al., "Effect of isotretinoin on interleukin-1α in acne patients" Southern China Journal of Dermato-Venereology vol. 12, Issue 1, pp. 52-53 (Mar. 30, 2005) with its ENG abstract (3 pages).

Eurasian Office Action for EA Application No. 201992544 mailed Dec. 28, 2021 (4 pages, with English Translation).

Mason et al., "Kinetics of the Reaction of a Myelin Basic Protein Peptide with Soluble IAu," Biochemistry, 1995, 34:14874-14878. (Year: 1995).

(Continued)

*Primary Examiner* — Julie Ha
(74) *Attorney, Agent, or Firm* — Merchant & Gould P.C.

(57) ABSTRACT

A compound comprising a structure in which isotretinoin is linked to a peptide via a covalent bond and an antibiotic, anti-inflammatory, or anti-oxidative pharmaceutical or cosmetic composition comprising the same. A compound having a structure in which isotretinoin is linked to a peptide via a covalent bond according to the present invention exhibits excellent physiological activity such as antibiotic, anti-inflammatory, or anti-oxidative actions, as well as having outstanding properties, such as solubility in water, etc., and thus can find useful applications in various fields including medicines, cosmetics, etc.

3 Claims, 9 Drawing Sheets

Specification includes a Sequence Listing.

(56) References Cited

FOREIGN PATENT DOCUMENTS

| WO | 03/037385 A1 | 5/2003 |
| WO | 2006/005455 A2 | 1/2006 |
| WO | 2015/174600 A1 | 11/2015 |

OTHER PUBLICATIONS

Matrixyl from https://pubchem.ncbi.nlm.nih.gov/compound/9897237, pp. 1-7, accessed Nov. 22, 2021. (Year: 2021).
Author Unknown, "Tech Tip #56—Calculate Reagent Log P Values To Determine Solubility Characteristics", Thermo Scientific, 2007, Thermo Fisher Scientific, Inc., 2 pages.
Office Action for ARIPO Patent Application No. AP/P/2019/012035 dated Jan. 23, 2021 (4 pages).
Layton, A, "The use of isotretinoin in acne," Dermato-Endocrinology, 1:3, 162-169. (Year: 2009).
Jung et al., Machine Translation of WO 2015174600, pp. 1-23. (Year: 2015).
Japanese Office Action for Japanese Patent Application No. 2019-561984 mailed Nov. 24, 2020, 4 pages.
Extended European Search Report from European Application No. 18797674.1, issued Apr. 2, 2020.
International Search Report from International Application No. PCT/KR2018/005447 (Feb. 7, 2019).
Written Opinion from International Application No. PCT/KR2018/005447 (Feb. 7, 2019).
Merrifield, "Solid Phase Peptide Synthesis. I. The Synthesis of a Tetrapeptide", J. Amer. Chem. Soc., 85:2149-54 (1963).
Yang et al., "Bioequivalence of NimegenTM Soft Capsule to RoAccutane® Soft Capsule (Isotretinoin 10 mg)", J. Kor. Pharm. Sci., vol. 37, No. 4, pp. 255-261 (2007).
Second Office Action issued on Dec. 9, 2023 for the corresponding Iranian patent application No. 139850140003007223 (14 pages including English Translation).

* cited by examiner

CONJUGATE OF ISOTRETINOIN AND PEPTIDE

CROSS-REFERENCE TO RELATED APPLICATION(S)

This application is a divisional application of U.S. application Ser. No. 16/612,125, filed Nov. 8, 2019, which is a U.S. National Stage Application of PCT/KR2018/005447, filed May 11, 2018, which claims benefit of Serial No. 10-2017-0058866, filed May 11, 2017 in the Republic of Korea and which applications are incorporated herein by reference. To the extent appropriate, a claim of priority is made to each of the above disclosed applications.

SEQUENCE STATEMENT

This application contains a Sequence Listing, which has been submitted electronically in ASCII format and is hereby incorporated by reference in its entirety. Said ASCII copy, created and filed in U.S. Ser. No. 16/612,125, is named 2020-05-04_Sequence Listing.txt and is 6,522 bytes (6.37 KB) in size.

TECHNICAL FIELD

The prevent invention relates to a compound having a structure in which isotretinoin and a peptide are linked to each other via a covalent bond, and the use thereof.

BACKGROUND ART

Isotretinoin (13-cis-retinoic acid), which is an oral drug mainly used to treat acne, is known as one of the most effective drugs for acne, especially very severe nodulocystic acne since it inhibits all of sebum secretion, comedo, acne bacteria *Propionibacterium acnes*, and hyperkeratosis pilaris and has anti-inflammatory effects (Korea Patent Laying-Open No. 2002-0033751). In addition, isotretinoin is rarely used for the prevention or treatment of certain skin cancers such as squamous cell carcinoma, or other cancers, and may be used to treat Harlequin ichthyosis and lamellar ichthyosis, which are one of the deadly skin diseases. Isotretinoin is a retinoid associated with vitamin A, which is naturally found in the body in small amounts, and its isomer tretinoin is also a therapeutic agent for acne.

It has been reported that isotretinoin's mechanism of action treats the symptoms of acne by normalizing the keratinization process of small follicular epithelium, reducing the number of sebocytes while reducing sebum synthesis, and reducing *Propionibacterium acnes*, a microorganism which causes inflammation of acne. Since isotretinoin is fat soluble, its solubility in water is low, its absorption is increased when ingested with food, and its fasting bioavailability is about 20%. It has been reported that the time to reach the highest blood concentration upon oral administration is about 2-4 hours, and at 6 hours after administration, the blood concentration of the active metabolite 4-oxo-isotretinoin is higher than the blood concentration of isotretinoin (SK Yang et al., J. Kor. Pharm. Sci., Vol. 37, No. 4, 255-261, 2007).

However, the use of such isotretinoin may cause side effects such as skin exfoliation, dermatitis, skin dryness, pruritus, and skin weakness, which can cause significant discomfort after application to the skin, and therefore users with sensitive skin often get damaged when using such a compound. In addition, since isotretinoin has a low solubility in water, it is necessary to add various organic solvents to solubilize it, which may add inconvenience to the composition containing isotretinoin.

Therefore, there is a need for the development of novel compounds that can improve the problems of isotretinoin as described above, in particular a low solubility in water and that can further enhance the physiological efficacy of isotretinoin.

DISCLOSURE

Technical Problem

The present invention is to improve the problems of the conventional isotretinoin as described above, and it is a technical object of the present invention to provide a substance which exhibits identical or superior physiological activity compared to that of the case where natural isotretinoin is present alone, while having excellent properties such as solubility in water.

Technical Solution

In order to achieve the above object, the present invention provides a compound having a structure in which isotretinoin and a peptide are linked to each other via a covalent bond.

According to an embodiment of the present invention, the peptide may consist of the sequence of 2 to 30, preferably 5 to 20, more preferably 8 to 15, more preferably 10 to 12 amino acids, but is not limited thereto.

According to another embodiment of the present invention, the peptide is preferably, but not limited to, a water-soluble peptide. According to a preferred embodiment of the present invention, it is preferred that the proportion of amino acids having a hydrophilic side chain in the water-soluble peptide is as high as 50% or more, preferably 60% or more, more preferably 70% or more, more preferably 80% or more, more preferably 90% or more, and most preferably 100%. According to another preferred embodiment of the present invention, the amino acid having a hydrophobic side chain in the water-soluble peptide is present in 5 or less, preferably 4 or less, more preferably 3 or less, more preferably 2 or less, more preferably 1 or less, and most preferably none.

According to another embodiment of the present invention, the peptide may be a peptide consisting of the amino acid sequence of SEQ ID NO: 1, but is not limited thereto.

In addition, the present invention provides an antibiotic, anti-inflammatory, or anti-oxidative pharmaceutical composition comprising any one of the compounds as described above.

In addition, the present invention provides an antibiotic, anti-inflammatory, or anti-oxidative cosmetic composition comprising any one of the compounds as described above.

According to an embodiment of the present invention, the cosmetic composition may have the formulation such as a skin softener, a nutrition lotion, a nutrition cream, a massage cream, an essence, an eye cream, a cleansing cream, a cleansing foam, a cleansing water, a pack, a spray, a powder, a hair tonic, a hair cream, a hair lotion, a hair shampoo, a hair rinse, a hair conditioner, a hair spray, a hair aerosol, a pomade, a sol-gel, an emulsion, an oil, a wax, and an aerosol, but is not limited thereto.

Advantageous Effects

The compound having a structure in which isotretinoin and a peptide are linked to each other via a covalent bond according to the present invention exhibits excellent physiological activities such as antibiotic, anti-inflammatory, or anti-oxidative actions, as well as having outstanding properties, such as solubility in water, and the like, and thus can be used in various fields such as medicines, cosmetics, and the like.

BEST MODE

Figure 1:
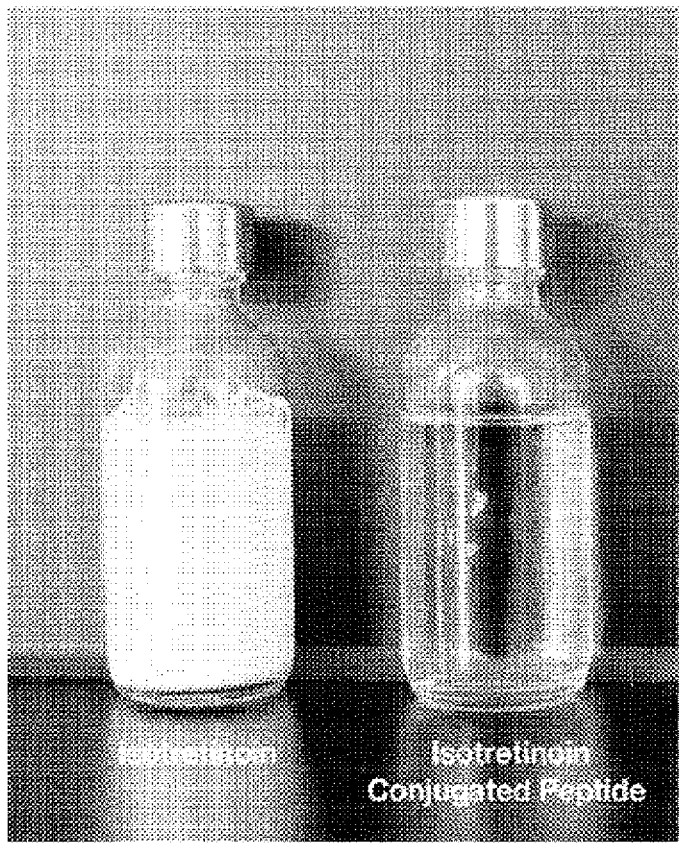
FIG. 1 is a photograph showing the solubility of the compounds according to the present invention and isotretinoin in water.

In order to achieve the above object, the present invention provides a compound having a structure in which isotretinoin and a peptide are linked to each other via a covalent bond.

The isotretinoin represents a 13-cis-retinoic acid having a chemical structure represented by the following chemical formula:

[Chemical Formula]

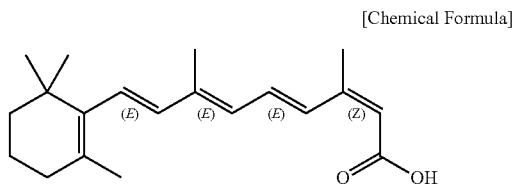 [SMILES: CC1=C(/C=C/C(C)=C/C=C/C(C)=C\C(=O)O)C(C)(C)CCC1]

As used herein, the term "peptide" refers to a linear molecule which is formed by linking amino acids to each other via a peptide bond. The peptides may be prepared according to conventional biological or chemical synthesis methods known in the art, in particular solid-phase synthesis techniques (Merrifield, *J. Amer. Chem. Soc.*, 85:2149-54 (1963); Stewart et al., Solid Phase Peptide Synthesis, 2nd ed., Pierce Chem. Co. Rockford, 111(1984)).

The peptide is preferably for increasing the water solubility of isotretinoin, and in this aspect, the peptide is preferably, but not limited to, a water soluble peptide. According to an embodiment of the present invention, the peptide may consist of the sequence of 2 to 30, preferably 5 to 20, more preferably 8 to 15, more preferably 10 to 12 amino acids. According to a preferred embodiment of the present invention, it is preferred that the proportion of amino acids having a hydrophilic side chain in the peptide is as high as 50% or more, preferably 60% or more, more preferably 70% or more, more preferably 80% or more, more preferably 90% or more, and most preferably 100%. On the other hand, it is preferred that the proportion of amino acids having a hydrophobic side chain in the peptide is as low as less than 50%, preferably 40% or less, more preferably 30% or less, more preferably 20% or less, more preferably 10% or less, and most preferably 0%. As used herein, the term "amino acids having a hydrophilic side chain" represents, but is not limited to, arginine (Arg), histidine (His), lysine (Lys), aspartic acid (Asp), glutamic acid (Glu), serine (Ser), threonine (Thr), asparagine (Asn), glutamine (Gln), cysteine (Cys), selenocysteine (Sec), glycine (Gly), and proline (Pro); the term "amino acids having a hydrophobic side chain" represents, but is not limited to, alanine (Ala), valine (Val), isoleucine (Ile), leucine (Leu), methionine (Met), phenylalanine (Phe), tyrosine (Tyr), and tryptophan (Trp); and, in addition to amino acids present in nature as described above, modifications thereof may be used without limitation. According to a preferred embodiment of the present invention, the amino acids having the hydrophobic side chain in the peptide are present in 5 or less, preferably 4 or less, more preferably 3 or less, more preferably 2 or less, more preferably 1 or less, and most preferably none. According to an embodiment of the present invention, the peptide is preferably, but not limited to, a peptide consisting of the amino acid sequences of SEQ ID NOs: 1 to 4.

Figure 2A:
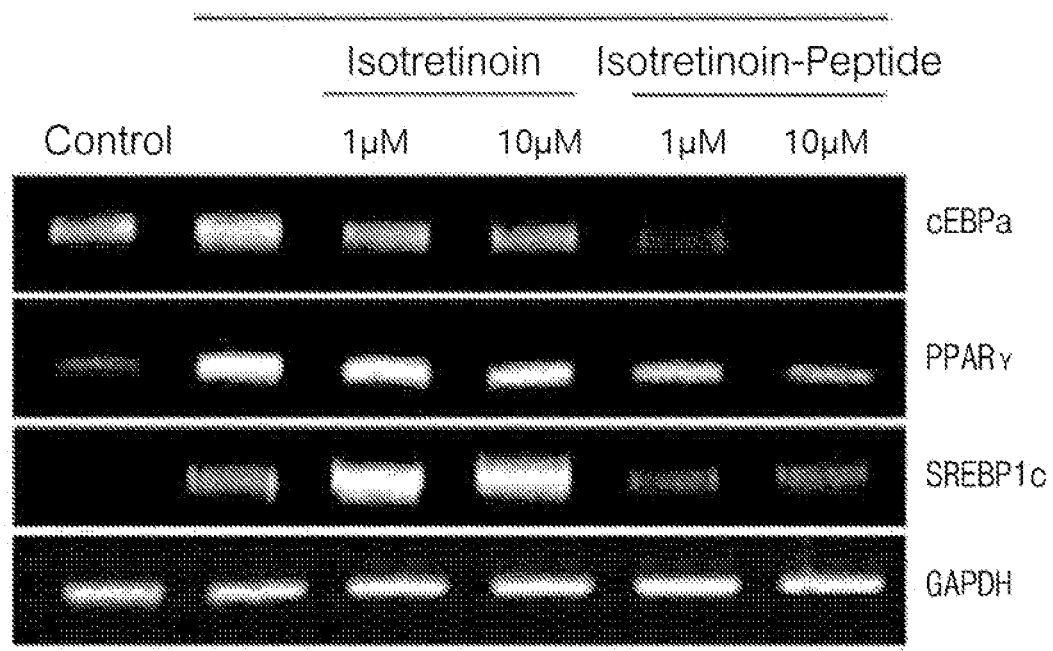
FIGS. 2A and 2B are RT-PCR and Western Blot photographs showing the effect of the compounds according to the present invention and isotretinoin on the expression of genes associated with sebum-forming signaling expressed in sebocytes.
Figure 2B:
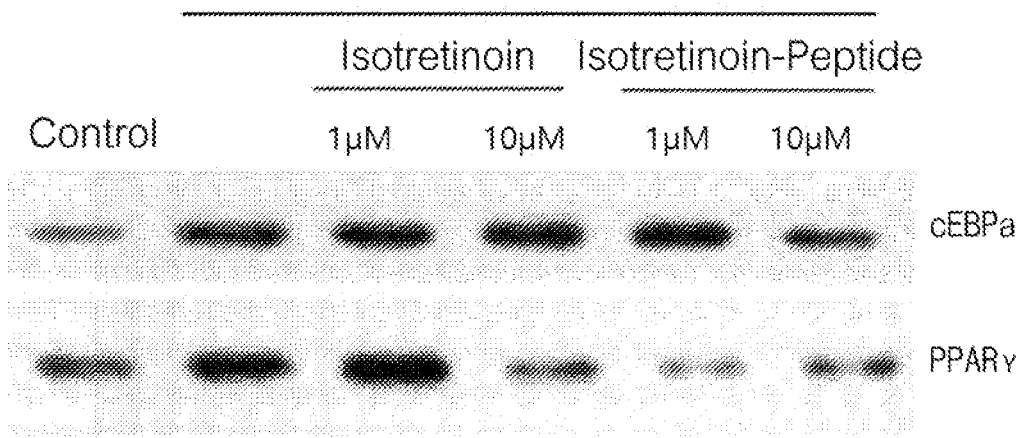
Figure 3A:
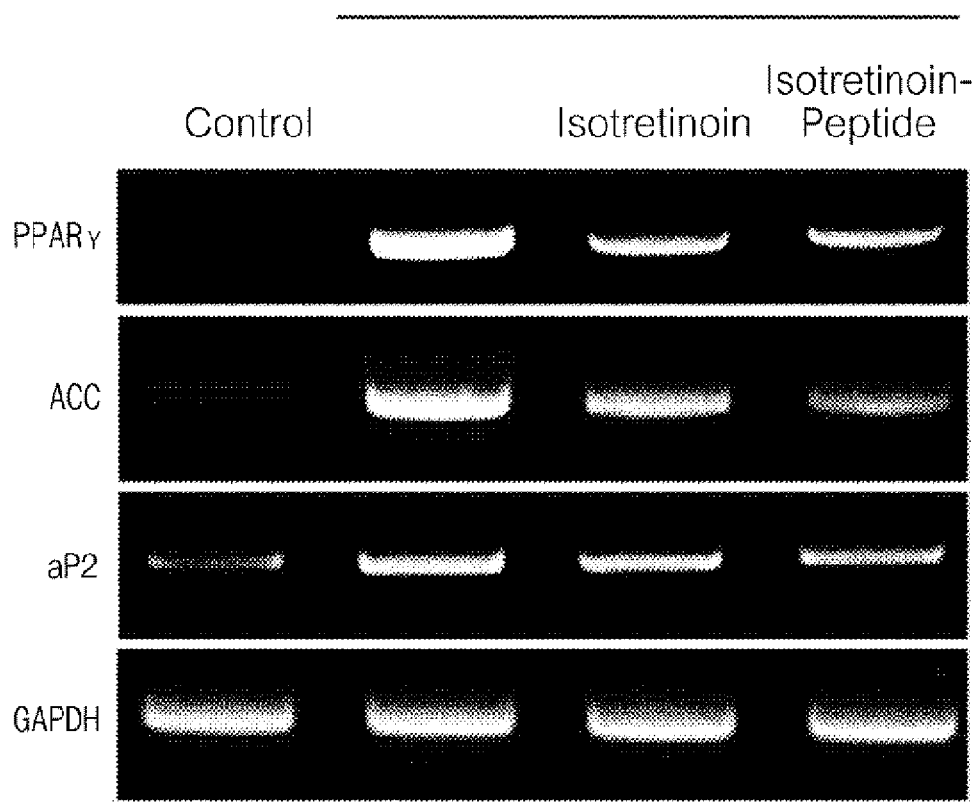
FIGS. 3A and 3B are RT-PCR and Oil Red O staining photographs showing the effect of the compounds according to the present invention and isotretinoin on the expression of genes associated with lipogenesis in 3T3 L1 preadipocytes.
Figure 7:
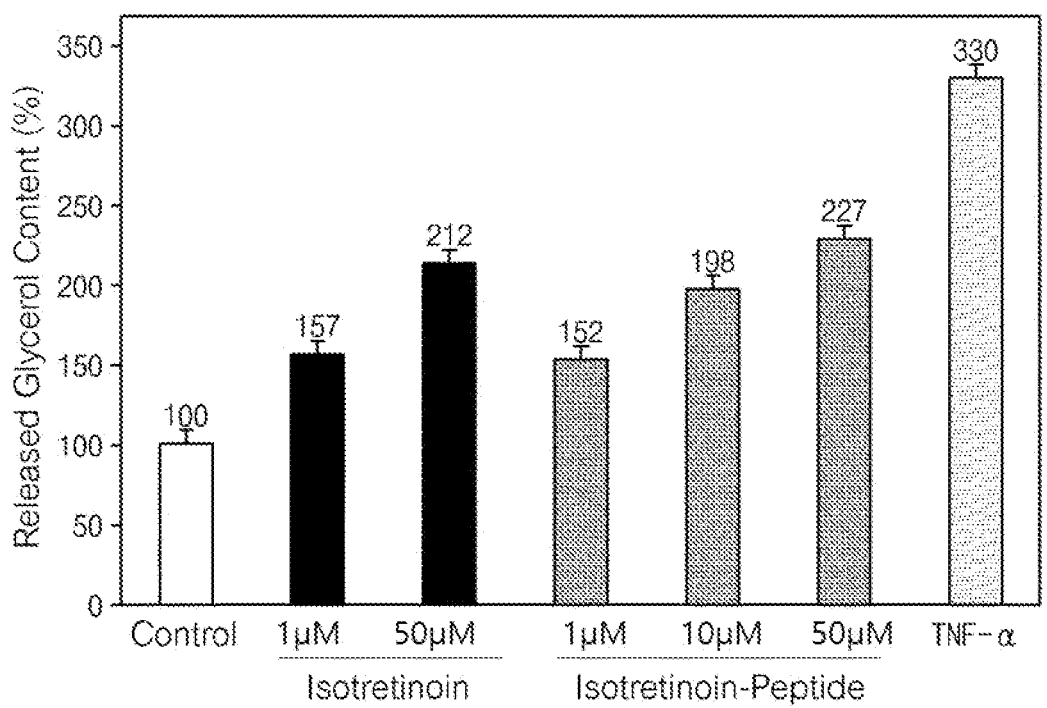
FIG. 7 is a graph showing the effect of the compounds according to the present invention and isotretinoin on the release of free glycerol in 3T3 L1 preadipocytes.
Figure 8A:
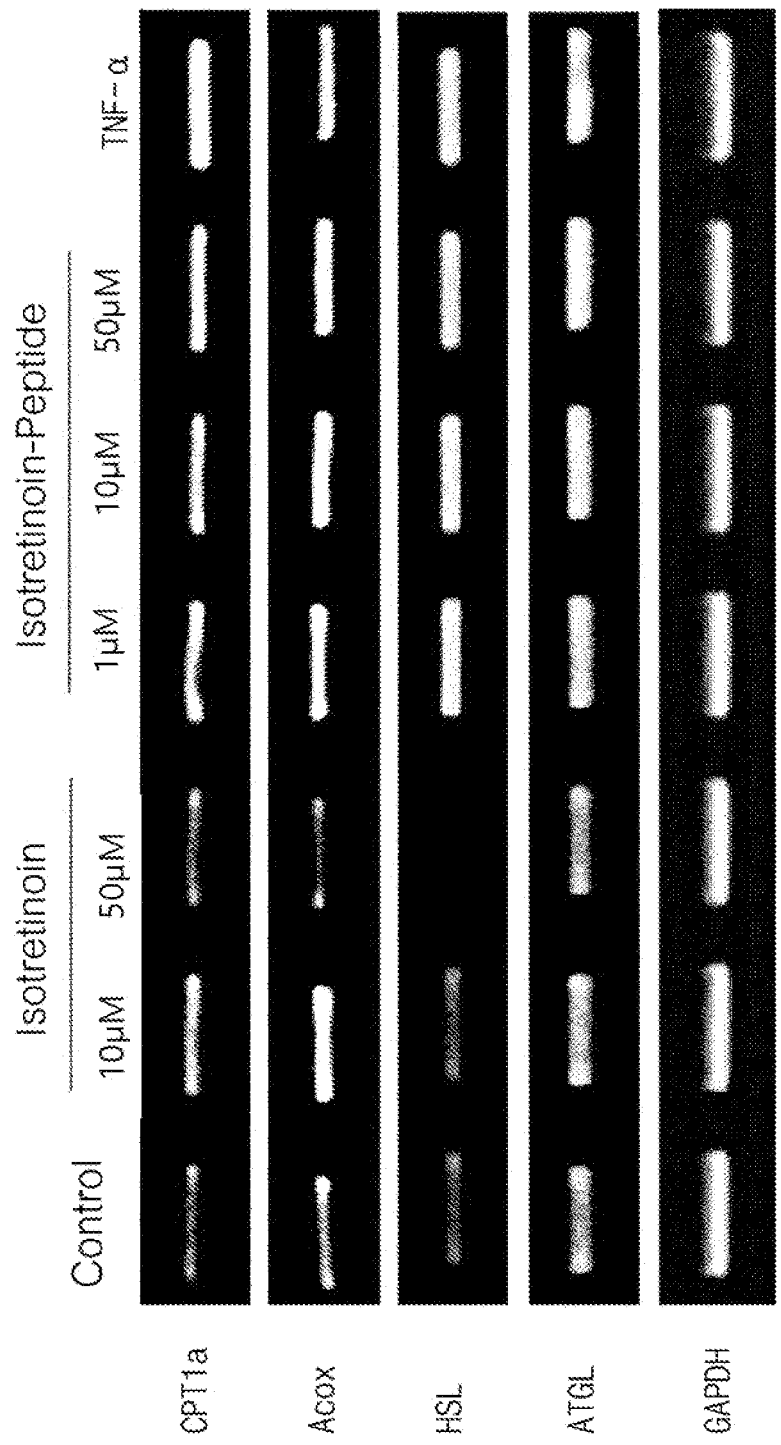
FIGS. 8A and 8B are RT-PCR and Oil Red O staining photographs showing the effect of the compounds according to the present invention and isotretinoin on the expression of genes associated with lipolysis in 3T3 L1 preadipocytes.
Figure 8B:
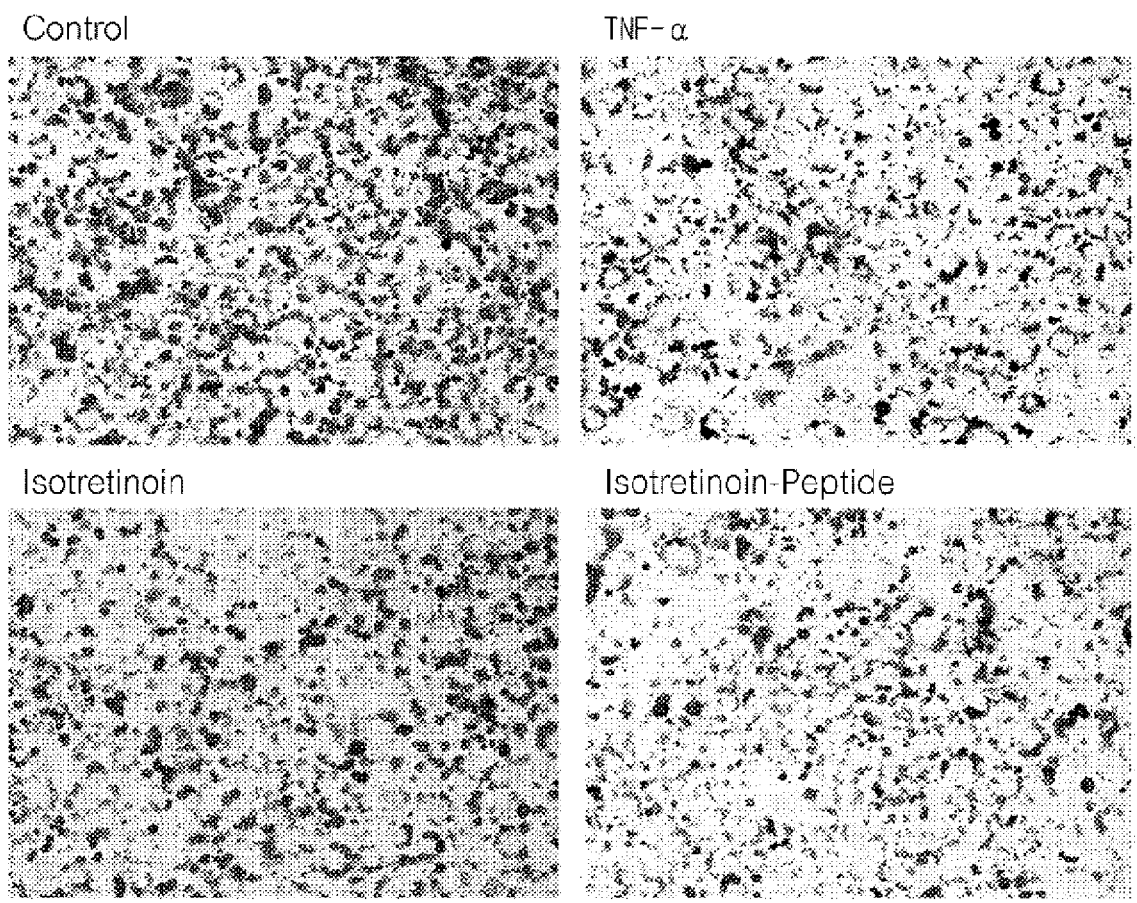

According to an embodiment of the present invention, the compounds of the present invention may have excellent solubility in water (see FIG. 1) and also remarkably reduce the expression of signaling genes and proteins associated with sebum formation (see FIGS. 2A and 2B). According to another embodiment of the present invention, the compounds of the present invention may remarkably reduce the expression of genes associated with lipogenesis and also reduce fat accumulation in the cells in a concentration-dependent manner (see FIGS. 3A and 3B). According to another embodiment of the present invention, the compounds of the present invention may remarkably reduce the expression of genes associated with inflammation and the formation of skin wrinkles, and the formation of intracellular reactive oxygen species (see FIGS. 4 to 6). According to another embodiment of the present invention, it was confirmed that in addition to the acne treatment effects of isotretinoin as known in the art, the compounds of the present invention may not only remarkably increase the release of glycerol due to lipolysis and the expression of genes associated with lipolysis, but also reduce fat accumulation in the cells (FIGS. 7, 8A, and 8B).

The compound of the present invention has excellent stability in itself, but may further improve stability by modifying any amino acid constituting the peptide bound to the compound. According to an embodiment of the invention, the N-terminus of the peptide may be combined with the protecting group selected from the group consisting of acetyl group, fluorenyl methoxy carbonyl group, formyl group, palmitoyl group, myristyl group, stearyl group, and polyethylene glycol (PEG) to further improve stability. According to another embodiment of the invention, the peptide may be combined with the protecting group selected from the group consisting of acetyl group, fluorenyl methoxy carbonyl group, formyl group, palmitoyl group, myristyl group, stearyl group, and polyethylene glycol (PEG) to further improve stability.

Modifications of amino acids as described above act to greatly improve the stability of the compounds of the present invention. As used herein, the term "stability" is used as a meaning encompassing not only "in vivo" stability but also "in vitro" stability such as storage stability (for example, room temperature storage stability). In addition, the above-mentioned protecting group acts to protect the compounds of the present invention against the attack of a protein cleaving enzyme in vivo and in vitro.

In addition, the present invention provides an antibiotic, anti-inflammatory, or anti-oxidative composition comprising the compound as an active ingredient. According to another embodiment of the present invention, the present invention provides a composition for improving skin condition comprising the compound as an active ingredient. In the present invention, the composition may be in the form of a pharmaceutical composition or cosmetic composition, but is not limited thereto. In addition, according to an embodiment of the present invention, improved skin conditions by the compounds of the present invention may be improved acne, improved wrinkle, improved skin elasticity, prevented skin aging, improved skin moisturization, removed wounds, or regenerated skin, but are not limited thereto.

Since the composition of the present invention comprises the compound of the present invention as described above as an active ingredient, the common content between the both is omitted in order to avoid excessive complexity of the present specification.

According to a preferred embodiment of the present invention, the composition of the present invention is a pharmaceutical composition comprising: (a) a pharmaceutically effective amount of the compound of the present invention as described above; and (b) a pharmaceutically acceptable carrier.

As used herein, the term "a pharmaceutically effective amount" means an amount sufficient to achieve the efficacy or activity of the compound of the invention as described above.

The pharmaceutically acceptable carriers comprised in the pharmaceutical composition of the present invention are those conventionally used in the formulation and include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil. The pharmaceutical composition of the present invention may further comprise a lubricant, a wetting agent, a sweetener, a flavoring agent, an emulsifier, a suspending agent, a preservative, and the like, in addition to the ingredients as described above. Suitable pharmaceutically acceptable carriers and agents are described in detail in Remington's Pharmaceutical Sciences (19th ed., 1995).

The pharmaceutical composition of the present invention may be prepared in a unit-dose form by formulating the compound of the present invention with a pharmaceutically acceptable carrier and/or excipient according to methods which may be easily carried out by those skilled in the art, or prepared by incorporating it into a multi-dose container. Wherein, the formulation may be in the form of a solution, suspension, or emulsion in an oil or aqueous medium, or in the form of an extract, a powder, a granule, a tablet, a capsule, or a gel (for example, a hydrogel), and may further comprise a dispersing agent and/or a stabilizer.

The pharmaceutical composition according to the present invention may be administered orally or parenterally in clinical administration and used in the form of general pharmaceutical formulation. That is, the pharmaceutical composition of the present invention may be administered in a variety of oral and parenteral formulations in actual clinical administration, and are prepared using diluents or excipients, such as a filler, an extender, a binder, a wetting agent, a disintegrating agent, and a surfactant, which are usually used when formulated. Solid formulations for oral administration include a tablet, a pill, a powder, a granule, a capsule, and the like, and such solid formulations are prepared by mixing at least one excipient such as starch, calcium carbonate, sucrose or lactose, and gelatin with the herbal extract or herbal fermentation product. In addition to simple excipients, lubricants such as magnesium stearate and talc are also used. Liquid formulations for oral administration include a suspension, a solution for internal use, an emulsion, and a syrup, and the like, and may include various excipients, such as a wetting agent, a sweetener, a flavoring agent, a preservative, and the like, in addition to commonly used simple diluents such as water and liquid paraffin. Formulations for parenteral administration include a sterile aqueous solution, a non-aqueous solution, a suspension, an emulsion, a lyophilized formulation, and a suppository. As the non-aqueous solvent and the suspension solvent, propylene glycol, polyethylene glycol, vegetable oils such as olive oil, injectable esters such as ethyl oleate, and the like may be used. As the base of the suppository, witepsol, macrogol, tween 61, cacao butter, laurin, glycerol, gelatin, and the like may be used.

The dosage unit may contain, for example, 1, 2, 3 or 4 times, or ½, ⅓ or ¼ times the individual dosage. Individual dosages contain an amount in which an active drug is administered at one time, and usually correspond to all, ½, ⅓ or ¼ times the daily dose.

The pharmaceutical composition of the present invention may be prepared in a unit-dose form by formulating the compound of the present invention with a pharmaceutically acceptable carrier and/or excipient according to methods which may be easily carried out by those skilled in the art, or prepared by incorporating it into a multi-dose container. Wherein, the formulation may be in the form of a solution, suspension, or emulsion in an oil or aqueous medium, or in the form of an extract, a powder, a granule, a tablet, a capsule, or a gel (for example, a hydrogel), and may further comprise a dispersing agent and/or a stabilizer.

According to a preferred embodiment of the present invention, the composition of the present invention may be a cosmetic composition comprising: (a) a cosmetically effective amount of the compound of the present invention as described above; and (b) a cosmetically acceptable carrier.

As used herein, the term "a cosmetically effective amount" means an amount sufficient to achieve the skin improving efficacy of the composition of the present invention as described above.

The cosmetic composition of the present invention may also be prepared in any formulations conventionally prepared in the art, and may be formulated into, for example, a solution, a suspension, an emulsion, a paste, a gel, a cream, a lotion, a powder, a soap, a surfactant-containing cleansing, an oil, a powder foundation, an emulsion foundation, a wax foundation, a spray, and the like, but is not limited thereto. More specifically, it may be prepared in various forms such as a skin softener, a nutrition lotion, a nutrition cream, a massage cream, an essence, an eye cream, a cleansing cream, a cleansing foam, a cleansing water, a pack, a spray, a powder, a hair tonic, a hair cream, a hair lotion, a hair shampoo, a hair rinse, a hair conditioner, a hair spray, a hair aerosol, a pomade, a gel, a sol-gel, an emulsion, an oil, a wax, an aerosol, and the like, but is not limited thereto.

When the formulation of the present invention is a paste, a cream, or a gel, animal oil, vegetable oil, wax, paraffin, starch, tragacanth, cellulose derivative, polyethylene glycol, silicone, bentonite, silica, talc, or zinc oxide, and the like may be used as the carrier ingredient.

When the formulation of the present invention is a powder or a spray, lactose, talc, silica, aluminum hydroxide, calcium silicate, or polyamide powder may be used as the carrier ingredient, and in particular in the case of a spray, a propellant such as chlorofluorohydrocarbon, propane/butane, or dimethyl ether may be further included, but is not limited thereto.

When the formulation of the present invention is a solution or an emulsion, a solvent, a solubilizer, or an emulsifier is used as the carrier ingredient, and, for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid ester of sorbitan may be used, but are not limited thereto.

When the formulation of the present invention is a suspension, liquid diluents such as water, ethanol, or propylene glycol, suspending agents such as ethoxylated isostearyl alcohol, polyoxyethylene sorbitol ester, and polyoxyethylene sorbitan ester, microcrystalline cellulose, aluminum metahydroxide, bentonite, agar, or tragacanth, and the like may be used as the carrier ingredient, but are not limited thereto.

When the formulation of the present invention is a surfactant-containing cleansing, aliphatic alcohol sulfate, aliphatic alcohol ether sulfate, sulfosuccinic acid monoester, isethionate, imidazolinium derivative, methyltaurate, sarcosinate, fatty acid amide ether sulfate, alkylamidobetaine, aliphatic alcohol, fatty acid glyceride, fatty acid diethanolamide, vegetable oil, lanolin derivative, or ethoxylated glycerol fatty acid ester, and the like may be used as the carrier ingredient, but are not limited thereto.

When the formulation of the present invention is a hair shampoo, the compounds of the present invention are mixed with base ingredients for formulating shampoos, such as thickeners, surfactants, viscosity modifiers, moisturizers, pH adjusters, preservatives, essential oils, and the like. CDE may be used as the thickeners; LES, an anionic surfactant, and cocobetaine, an amphoteric surfactant may be used as the surfactants; polyquater may be used as the viscosity modifiers; glycerin may be used as the moisturizers; citric acids and sodium hydroxides may be used as the pH adjusters; grapefruit extracts may be used as the preservatives; in addition, essential oils such as cedarwood, peppermint, rosemary and the like, silkamino acid, pentaol, vitamin E may be added. According to an embodiment of the present invention, the compound of the present invention as described above may be mixed with 5 to 10 parts by weight of CDE, 30 to 40 parts by weight of LES, 10 to 20 parts by weight of cocobetaine, 0.1 to 0.2 parts by weight of polyquarter, 5 to 10 parts by weight of glycerin, 0.1 to 1.01 parts by weight of grapefruit extract, 0.5 to 1 part by weight of silk amino acid, 0.5 to 1 part by weight of pentaol, 0.5 to 2 parts by weight of vitamin E, and 0.01 to 0.1 parts by weight of any one of cedarwood, peppermint, and rosemary as essential oils, based on 100 parts by weight of the compound of the present invention, but is not limited thereto.

The ingredients included in the cosmetic composition of the present invention comprise ingredients conventionally used in cosmetic compositions in addition to the compound of the present invention as an active ingredient and the carrier ingredients, and may comprise conventional adjuvants such as, for example, an antioxidant, a stabilizer, a solubilizer, a vitamin, a pigment, and a perfume, but are not limited thereto.

EXAMPLES

Hereinafter, the present invention will be described in detail through examples.

However, the following examples are only for illustrating the present invention, and the content of the present invention is not limited to the following examples.

Example 1. Synthesis of Compounds of Present Invention

<1-1> Synthesis of Peptides of SEQ ID NO: 1

700 mg of chlorotrityl chloride resin (CTL resin; Nova biochem [0064] Cat No. 01-64-0021) was placed in a reaction vessel, and then 10 ml of methylene chloride (MC) was added thereto and stirred for 3 minutes. After removal of the solution, 10 ml of dimethylformamide (DMF) was added thereto and stirred for 3 minutes, and then the solvent was removed again. 10 ml of a dichloromethane solution was placed in the reactor, and subsequently 200 mmol Fmoc-Met-OH (Bachem, Swiss) and 400 mmol diisopropylethylamine (DIEA) were placed therein and stirred to be well dissolved, and then reaction was carried out with stirring for 1 hour. After completion of the reaction, washing was performed, and methanol and DIEA (2:1) were dissolved in dichloromethane (DCM) and reacted for 10 minutes, and then washing was performed with an excess of DCM/DMF (1:1). Thereafter, the solution was removed, 10 ml of dimethylformamide (DMF) was placed therein and stirred for 3 minutes, and then the solvent was removed again. 10 ml of a deprotecting solution (20% piperidine/DMF) was placed in the reaction vessel and stirred at room temperature for 10 minutes, and then the solution was removed. Thereafter, the same amount of deprotecting solution was placed therein to maintain the reaction for 10 minutes again, and then the solution was removed, and washing was performed twice with DMF, once with MC, and once with DMF for 3 minutes, respectively, to give Met-CTL resins.

10 ml of a DMF solution was placed in a new reactor, and 200 mmol Fmoc-Val-OH (Bachem, Swiss), 200 mmol HoBt, and 200 mmol Bop were placed therein, and then well dissolved by stirring. 400 mmol DIEA was placed in the reactor twice in fractions and stirred for at least 5 minutes until all solids dissolved. The dissolved amino acid mixture solution was placed in the reaction vessel containing the deprotected resins, and reacted with stirring at room temperature for 1 hour. The reaction solution was removed and stirred three times for each 5 minutes with a DMF solution, and then removed. A small amount of the reacted resin was taken and the degree of reaction was checked using a Kaiser test (Ninhydrin Test). The deprotection reaction was performed twice as described above with the deprotecting solution to prepare a Val-Met-CTL resin. The resin was sufficiently washed with DMF and MC, and subjected to the Kaiser test once again to perform an amino acid attachment experiment below in the same manner as described above.

Based on selected amino acid sequences, chain reaction was performed in order of Fmoc-Leu, Fmoc-Phe, Fmoc-Asn (Trt), Fmoc-Ala, Fmoc-Asn(Trt), Fmoc-Thr(tBu), Fmoc-Arg(Pbf), Fmoc-Asp(tBu), Fmoc-Ile, Fmoc-Leu, Fmoc-Arg (Pbf), and Fmoc-Arg(Pbf). The Fmoc-protecting group was reacted with a deprotecting solution twice for 10 minutes, and then washed well and removed. After acetic anhydride, DIEA, and HoBt were placed therein to perform acetylation for 1 hour, the prepared peptidyl resin was washed three times with DMF, MC, and methanol, respectively, and dried by slowly flowing nitrogen air, and then completely dried under reduced pressure vacuum over $P_2O_5$, 30 ml of a leaving solution (95% of trifluoroacetic acid, 2.5% of distilled water, and 2.5% of thioanisole) was placed therein, and the reaction was maintained for 2 hours while shaking at room temperature occasionally. The resin was filtered by filtration and washed with a small volume of TFA solution, and then was combined with the mother liquor. The distillation was carried out using a reduced pressure so that the total volume is remained to be half, and 50 ml of cold ether was added thereto to induce precipitation, which centrifuged to collect the precipitate and washed twice more with cold ether. After removing the mother liquor and sufficiently drying under a nitrogen atmosphere, 1.49 g of the pre-purified peptide NRRLIDRTNANFLVM (SEQ ID NO: 1) was synthesized (yield: 86.5%). The molecular weight of 1719.1 (theoretical value: 1719.2) was obtained when measured using the molecular weight measuring instrument.

TABLE 1

| SEQ ID NO | Amino Acid Sequence | Analytical Value (Mass Spectrometer) | |
|---|---|---|---|
| | | Analytical Value | Theoretical Value |
| 1 | RRLIDRTNANFLVM | 1719.1 | 1719.2 |

<1-2> Synthesis of Compounds of Present Invention

Deprotected peptide (1 mmol) and 10 ml of dimethylformamide (DMF) were placed in a peptide reactor, and then 270 mg (2.0 equivalents) of 1-hydroxybenzotriazole (HOBt), 1.04 g (2.0 equivalents) of (benzotriazol-1-yloxy)tripyrrolidino postponium hexafluorphosphonate (PyBOP), and 277 mg (2.0 equivalent) of isotretinoin were added thereto and reacted for 30 minutes. 388 mg (3 equivalents) of N,N-diisopropylethylamine (DIEA) was added thereto and reacted at room temperature for 2 to 4 hours, and then recrystallization was performed using 10 ml (10 mmol) of diethyl ether and filtration was performed to obtain a hybrid peptide.

Experimental Example 1. Solubility Test of Compounds of Present Invention

The isotretinoin-peptide compound prepared in Example <1-2> above and isotretinoin were dissolved in distilled water at a concentration of 10 mg/ml, respectively.

As a result, in contrast to isotretinoin itself is hardly dissolved in water, it was confirmed that the isotretinoin-peptide compound of the present invention was completely dissolved in water (FIG. 1).

Experimental Example 2. Inhibitory Effect of Compounds of Present Invention on Expression of Sebum-Forming Signaling Genes RT-PCR analysis was performed to confirm the effect of the isotretinoin-peptide compound of the present invention synthesized in Example <1-2> on the expression of signaling genes associated with sebum formation. Specifically, sebocytes were stimulated by treatment with 100 μM arachidonic acid as a stimulant, subsequently treated with 1 or 10 μM isotretinoin-peptide compound of the present invention or isotretinoin, and cultured for 24 hours, and then, RNA was isolated from the cultured cells in the manner as described below, and the effect of the compounds on the expression of the signaling molecules cEBPα, PPARγ, and SREBP1c involved in sebum formation was confirmed using the primers described in Table 2 below. RNA extraction kit (Qiagen RNeasy kit) was used to extract the total RNA of the cells, and then 3 μg of RNA, 2 μg of random hexamer, and DEPC-treated water were added thereto and reacted at 65° C. for 5 minutes to synthesize single-stranded DNA from RNA. 5× first-strand buffer, 0.1 M DTT, 10 mM dNTP, and reverse transcriptase were placed therein to make a total of 20 ml, and reacted at 42° C. for 1 hour. After heating at 95° C. for 5 minutes again, 20 ml of distilled water was added thereto to make a final 40 ml of cDNA. Polymerase chain reaction (PCR) was performed by mixing 10 pmol primer, 10× Taq buffer, 10 mM dNTP, and i-Taq DNA polymerase as shown in Table 2 below, specific for each of 3 μl of cDNA, cEBPα, PPARγ, SREBP1c, and GAPDH genes. PCR reaction condition was 30 seconds at 94° C., 30 seconds at 55-56° C., and 30 seconds at 72° C. Cycle number genes were analyzed under conditions in which PCR results could be exponentially amplified. 5 ml of the obtained PCR product was electrophoresed on 1% agarose gel and stained with ethidium bromide to confirm the mRNA levels of the sebum-forming signaling genes cEBPα, PPARγ, and SREBP1c.

TABLE 2

| Factor | | | Primer Sequence | | SEQ ID NO |
|---|---|---|---|---|---|
| cEBP α | Forward | (5') | TCGGTGGACAAGAACAGCAA | (3') | 2 |
| | Reverse | (5') | CCTTGACCAAGGAGCTCTCA | (3') | 3 |
| PPAR γ | Forward | (5') | TTCGCTGATGCACTGCCTAT | (3') | 4 |
| | Reverse | (5') | ACAGACTCGGCACTCAATGG | (3') | 5 |
| SREBP1c | Forward | (5') | GACCGACATCGAAGGTGAAG | (3') | 6 |
| | Reverse | (5') | AAGAGAGGAGCTCAATGTGGC | (3') | 7 |
| GAPDH | Forward | (5') | GGAGCCAAAAGGGTCATCAT | (3') | 8 |
| | Reverse | (5') | GTGATGGCATGGACTGTGGT | (3') | 9 |

In addition, sebocytes were stimulated by treatment with acne bacteria Propionibacterium acnes (100 μg/ml) as a stimulant for 48 hours, subsequently treated with 1 or 10 μM isotretinoin-peptide compound of the present invention or isotretinoin, and the expression of the signaling proteins CEBPα and PPARγ associated with sebum formation was confirmed by Western blot analysis. As a result, it was confirmed that the compound having a structure in which isotretinoin and a peptide are linked to each other via covalent bond according to the present invention could more remarkably reduce the expression of signaling genes and proteins associated with sebum formation even at a much lower concentration, compared to isotretinoin (FIGS. 2A and 2B).

Experimental Example 3. Inhibitory Effect of Compounds of the Present Invention on Lipogenesis RT-PCR analysis was performed to confirm the effect of the isotretinoin-peptide compound of the present invention synthesized in Example <1-2> on the expression of genes associated with lipogenesis. Specifically, 3T3 L1 preadipocytes were inoculated into 24-well plates at $2 \times 10^4$ cells/well and cultured, and then exchange with a differentiation medium containing 0.5 mM IBMX, 0.25 μM dexamethasone, and 1 μg/ml insulin was made and the cells were cultured for 10 days with 10 μM of the isotretinoin-peptide compound of the present invention or isotretinoin, and then, the effects of the compounds on the expression of PPARγ, ACC, and aP2 genes involved in lipogenesis were confirmed. To this end, RT-PCR was performed in the same manner as in Experimental Example 2 above, except that the primers as shown in Table 3 below were used as primers specific for PPARγ, ACC, and aP2.

TABLE 3

| Factor | | Primer Sequence | SEQ ID NO |
|---|---|---|---|
| PPAR γ | Forward (5') | TTCGCTGATGCACTGCCTAT (3') | 4 |
| | Reverse (5') | ACAGACTCGGCACTCAATGG (3') | 5 |
| ACC | Forward (5') | GAATGTTTGGGGATATTTCAG (3') | 10 |
| | Reverse (5') | TTCTGCTATCAGTCTGTCCAG (3') | 11 |
| aP2 | Forward (5') | CATCAGCGTAAATGGGGATT (3') | 12 |
| | Reverse (5') | ACACATTCCACCACCAGCTT (3') | 13 |

Figure 3B:
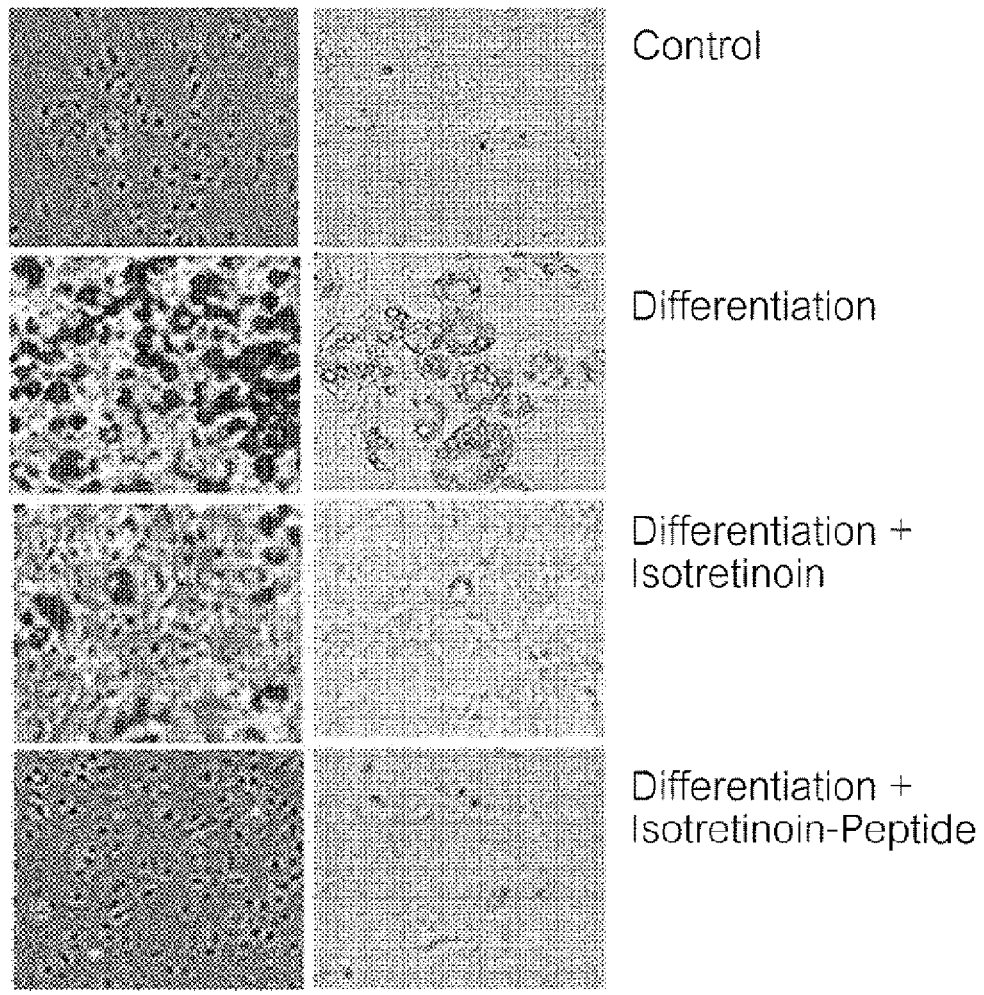

In addition, in order to measure the effect of inhibiting fat accumulation by the isotretinoin-peptide compound of the present invention, 3T3-L1 cells were inoculated into 24-well plates at $2 \times 10^4$ cells/well and cultured, and then exchange with a differentiation medium containing 10 μg/ml insulin, 0.1 μM dexamethasone, and 0.5 μM IBMX was made and the cells were treated with the isotretinoin-peptide compound of the present invention or isotretinoin. Thereafter, exchange with a medium containing 10 μg/ml insulin was made every 2 days, and an Oil Red O staining analysis was performed on day 9 of differentiation induction. To this end, the cells were washed with PBS, and then fixed by treatment with 4% paraformaldehyde for 10 minutes, washed with distilled water, and then incubated with 60% isopropanol for 5-10 minutes. The fixed cells were stained with Oil Red solution [1% Oil Red in isopropanol was diluted in $dH_2O$ at a volume ratio of 6:4] for 30 minutes, and then washed again with PBS. The stained cells were observed under an optical microscope, and then washed with distilled water, mixed with 1 ml of 100% isopropanol at 4° C., and then quantified at a wavelength of 510 nm the next day. As a result, it was confirmed that the compound having a structure in which isotretinoin and a peptide are linked to each other via covalent bond according to the present invention remarkably reduced the expression of genes associated with lipogenesis (FIG. 3A) compared to isotretinoin and also decreased the degree of intracellular fat accumulation dependent on the compound (FIG. 3B).

Experimental Example 4. Inhibitory Effect of Compounds of Present Invention on Inflammation RT-PCR analysis was performed to confirm the effect of the isotretinoin-peptide compound of the present invention synthesized in Example <1-2> on inflammation induced by acne bacteria. Specifically, 300,000 cells of HaCaT keratinocytes were inoculated into each well of 6-well plates, and then cultured in DMEM culture broth (Gibco, USA) containing 10% FBS for 24 hours under 37° C. and 5% $CO_2$. After exchange with a fresh medium was made, the cells were treated with 50 μg/ml acne bacteria (P. acnes), 50 μM salicylic acid, and 10 μM or 50 μM CG-Dinfla, and the treated acne bacterium was treated with the isotretinoin-peptide compound of the present invention and isotretinoin used as a positive control group at a concentration of 1 or 10 μM, and then cultured for 24 hours under the same conditions as described above, and then the effects of the compounds on the expression of IFN-γ, IL-1β, IL-6, IL-17A, and TNF-α genes involved in inflammation formation were confirmed. To this end, RT-PCR was performed in the same manner as in Experimental Example 2 above, except that the primers as shown in Table 4 below were used as primers specific for IFN-γ, IL-1β, IL-6, IL-17A, and TNF-α.

TABLE 4

| Factor | | Primer Sequence | SEQ ID NO |
|---|---|---|---|
| IFN-γ | Forward (5') | GAGGTCAACAACCCACAGGT (3') | 14 |
| | Reverse (5') | GGGACAATCTCTTCCCCACC (3') | 15 |
| IL-1β | Forward (5') | TTCGACACATGGGATAACGA (3') | 16 |
| | Reverse (5') | TCTTTCAACACGCAGGACAG (3') | 17 |
| IL-6 | Forward (5') | AAAGAGGCACTGCCAGAAAA (3') | 18 |
| | Reverse (5') | ATCTGAGGTGCCCATGCTAC (3') | 19 |
| IL-17A | Forward (5') | GGTCAACCTCAAAGTCTTTAACTC (3') | 20 |
| | Reverse (5') | TTAAAAATGCAAGTAAGTTTGCTG (3') | 21 |
| TNF-α | Forward (5') | AACATCCAACCTTCCCAAACG (3') | 22 |
| | Reverse (5') | GACCCTAAGCCCCCAATTCTC (3') | 23 |

Figure 4:
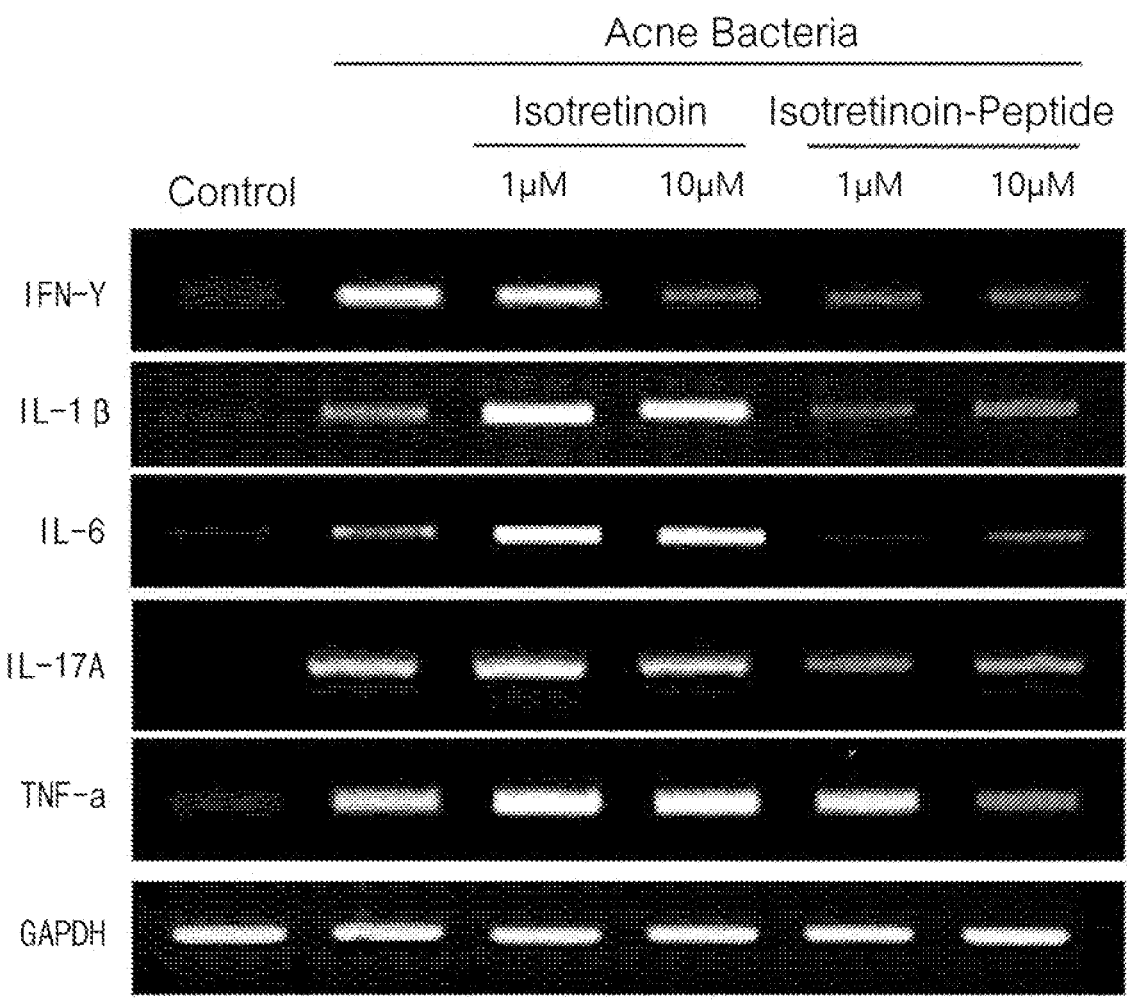
FIG. 4 is a RT-PCR electrophoresis photograph showing the effect of the compounds according to the present invention and isotretinoin on the expression of genes associated with inflammation in HaCaT keratinocytes.

As a result, it was confirmed that the compound having a structure in which isotretinoin and a peptide are linked to each other via covalent bond according to the present invention could more remarkably reduce the expression of genes associated with inflammation formation even at a much lower concentration, compared to isotretinoin (FIG. 4).

Experimental Example 5. Inhibitory Effect of Compounds of Present Invention on MMP Activity The effect of the isotretinoin-peptide compound of the present invention synthesized in Example <1-2> on MMP activity induced by acne bacteria was confirmed. Specifically, the HaCaT keratinocytes were cultured, and then the cells were pretreated with 1 or 10 μM isotretinoin-peptide compound of the present invention or isotretinoin, and 30 minutes later, treated with acne bacteria (P. acnes) as a stimulant. The culture broth was collected after 48 hours of culture, and the culture broth and the zymography buffer (Sigma Aldrich) were reacted in a 1:1 ratio, and then 20 μl of the reaction solution was electrophoresed on 8% sodium dodecylsulfate-polyacrylamide gel electrophoresis (SDS-PAGE) (10% gelatin). Thereafter, the gel was washed three times for 10 minutes in 0.1% Triton X-100 buffer (Sigma Aldrich), activated in TNCB buffer (Sigma Aldrich), and stained with Coomassie blue, and then the intensity of the band was measured.

Figure 5:
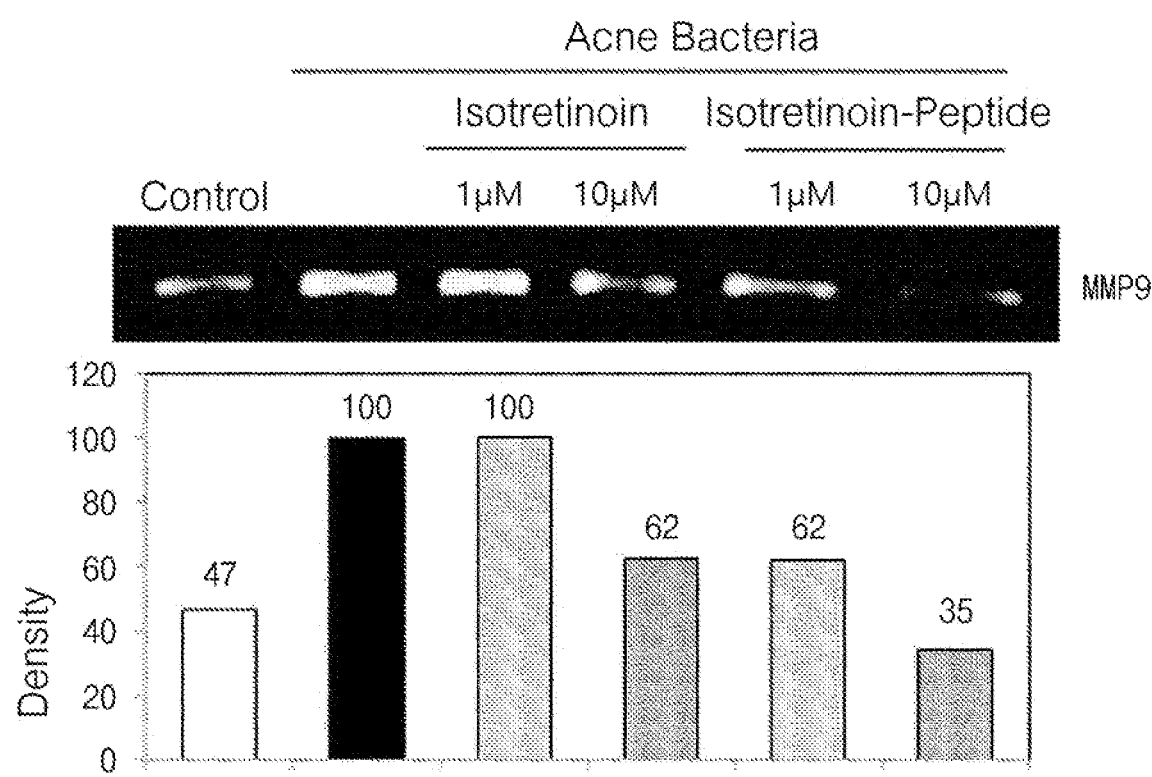
FIG. 5 is an electrophoretic photograph and a graph showing the effect of the compounds according to the present invention and isotretinoin on the activity of matrix metalloproteinase (MMP) in HaCaT keratinocytes.

As a result, it was confirmed that the compound having a structure in which isotretinoin and a peptide are linked to each other via covalent bond according to the present invention could more remarkably reduce the expression of the MMP-9 gene associated with the formation of skin wrinkles even at a much lower concentration, compared to isotretinoin (FIG. 5).

Experimental Example 6. Inhibitory Effect of Compounds of Present Invention on Intracellular Reactive Oxygen Species The effect of the isotretinoin-peptide compound of the present invention synthesized in Example <1-2> on the formation of intracellular reactive oxygen species (ROS) induced by acne bacteria was confirmed. Specifically, sebocytes were inoculated into 6-well plates at $1 \times 10^6$ cells/well and cultured overnight. The cells were pretreated with the isotretinoin-peptide compound of the present invention or isotretinoin, and 30 minutes later, treated with acne bacteria (*P. acnes*) as a stimulant at a concentration of 100 μg/ml and cultured for 48 hours. The cells were treated with DCF-DH, and 30 minutes later, oxidative activity was measured by the degree of fluorescence using FACS.

Figure 6:
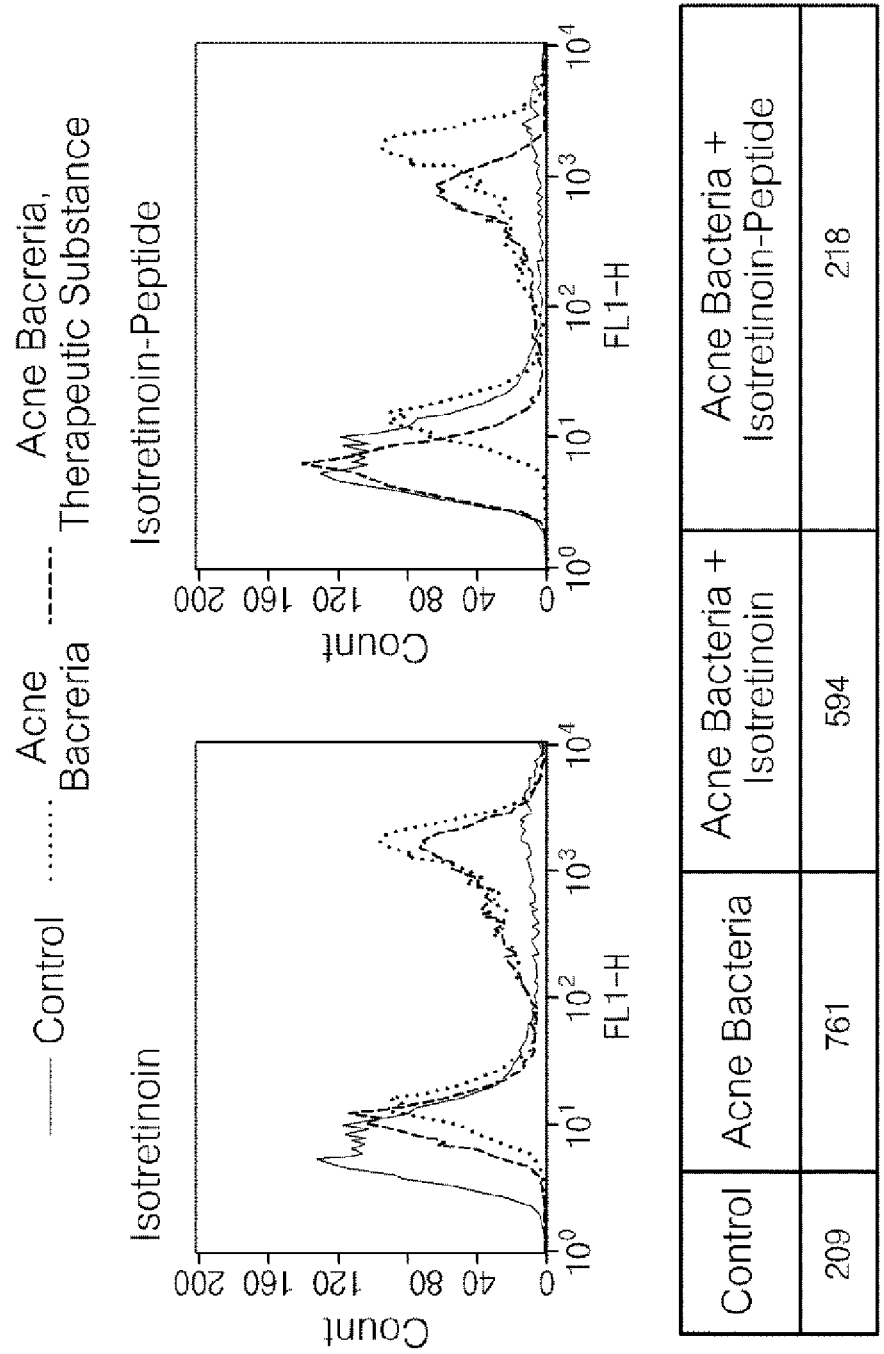
FIG. 6 is a graph showing the effect of the compounds according to the present invention and isotretinoin on the content of intracellular reactive oxygen species in sebocytes.

As a result, it was confirmed that the compound having a structure in which isotretinoin and a peptide are linked to each other via covalent bond according to the present invention could more remarkably reduce the formation of intracellular ROS induced by acne bacteria, compared to isotretinoin (FIG. 6).

Experimental Example 7. Effect of Compounds of Present Invention on Lipolysis (1)

Adipocytes store extra energy in the form of neutral fats in lipid droplets, but when energy is needed, they are broken down into fatty acids and glycerol by enzymes such as adipose triglyceride lipase, HSL, and monoglyceride lipase to produce energy or to be used for cell signaling or fat synthesis. Thus, the present inventors performed the release of free glycerol and analysis of intracellular triglycerol content in order to confirm the effect of the isotretinoin-peptide compound of the present invention synthesized in Example <1-2> on lipolysis. Specifically, 3T3-L1 cells were inoculated into 24-well plates at $2 \times 10^4$ cells/well (DMEM, 10% BCS) and cultured for 2 days. Exchange with DMEM medium containing 10% FBS was made, and then the cells were cultured for 2 days and further cultured for 2 days in DMEM (10% FBS) containing 0.5 mM IBMX, 0.25 μM dexamethasone, and 10 μg/ml insulin. Thereafter, the cells were cultured for 2 days in DMEM (10% FBS) containing 1 μg/ml insulin, and then cultured again for 3 days in DMEM (10% FBS) containing 1 μg/ml insulin. When exchange with FBS medium was made, the cells were treated with the isotretinoin-peptide compound of the present invention or isotretinoin, and culture broth was collected on day 8 of differentiation to perform glycerol analysis using a glycerol colorimetric analysis kit (Cayman).

As a result, the compound having a structure in which isotretinoin and a peptide are linked to each other via covalent bond according to the present invention remarkably increased the release of glycerol due to lipolysis, compared to isotretinoin (FIG. 7).

Experimental Example 8. Effect of Compounds of Present Invention on Lipolysis (2)

RT-PCR analysis and Oil Red O staining were performed in the same manner as described in Experimental Example 3 to confirm the effect of the isotretinoin-peptide compound of the present invention synthesized in Example <1-2> on the expression of genes associated with lipolysis. Wherein, CPT1a, Acox, HSL, and ATGL were used as genes involved in lipolysis, and primers as shown in Table 5 below were used as primers specific to the genes. In the case of TNF-α used as a control group, its lipolytic effect is generally known and it has the function such as phosphorylation of the lipolytic factor HSL and increased expression of ATGL, and thus was used as a control group to compare the effects of the compounds of the present invention.

TABLE 5

| Factor | | | Primer Sequence | | SEQ ID NO |
|---|---|---|---|---|---|
| CPT1a | Forward | (5') | CGTACCAAGTAGCCAAGGCA | (3') | 24 |
| | Reverse | (5') | CAGGAACGCACAGTCTCAGT | (3') | 25 |
| Acox | Forward | (5') | CCGCCGAGAGATCGAGAAC | (3') | 26 |
| | Reverse | (5') | CAGTTGCCTGGTGAAGCAAG | (3') | 27 |
| HSL | Forward | (5') | GGACACACACACACCTG | (3') | 28 |
| | Reverse | (5') | CCCTTTCGCAGCAACTTTAG | (3') | 29 |
| ATGL | Forward | (5') | TCGTGGATGTTGGTGGAGCT | (3') | 30 |
| | Reverse | (5') | TGTGGCCTCATTCCTCCTA | (3') | 31 |

As a result, it was confirmed that the compound having a structure in which isotretinoin and a peptide are linked to each other via covalent bond according to the present invention could remarkably increase the expression of genes associated with lipolysis compared to isotretinoin (FIG. 8A) and also reduce intracellular fat accumulation (FIG. 8B).

Formulation Example 1. Skin Softener

A skin softener comprising the compound of the present invention prepared in Example <1-2> above and consisting of the composition below was prepared according to the general method for preparing lotions.

TABLE 6

| Ingredient | Content (wt %) |
|---|---|
| Compound of the present invention | 2.5 |
| 1,3-Butylene glycol | 6 |
| Glycerine | 4 |
| PEG 1500 | 1 |
| Sodium hyaluronate | 1 |
| Polysorbate 20 | 0.5 |
| Ethanol | 8 |
| Preservative, pigment | adequate amount |
| Benzophenone-9 | 0.05 |
| Fragrance | very small amount |
| purified water | remaining amount |
| Sum | 100 |

Formulation Example 2. Nutrition Cream

A nutrition cream comprising the compound of the present invention prepared in Example <1-2> above and consisting of the composition below was prepared according to the general method for preparing nutrition creams.

TABLE 7

| Ingredient | Content (wt %) |
|---|---|
| Compound of the present invention | 2.5 |
| Meadowfoam oil | 3 |
| Cetearyl alcohol | 1.5 |
| Stearic acid | 1.5 |
| Glyceryl stearate | 1.5 |
| Liquid paraffin | 10 |
| Beeswax | 2 |
| Polysorbate 60 | 0.6 |
| Sorbitan sesquioleate | 2.5 |
| Squalane | 3 |
| 1,3-Butylene glycol | 3 |
| Glycerine | 5 |
| Triethanolamine | 0.5 |
| Tocopheryl acetate | 0.5 |
| Preservative, pigment | adequate amount |
| Fragrance | adequate amount |
| Purified water | remaining amount |
| Sum | 100 |

Formulation Example 3. Nutrition Lotion

A nutrition lotion comprising the compound of the present invention prepared in Example <1-2> above and consisting of the composition below was prepared according to the general method for preparing lotions.

TABLE 8

| Ingredient | Content (wt %) |
|---|---|
| Compound of the present invention | 2.5 |
| 1,3-Butylene glycol | 4 |
| Glycerine | 4 |
| Cetearyl alcohol | 0.8 |
| Glyceryl stearate | 1 |
| Triethanolamine | 0.13 |
| Tocopheryl acetate | 0.3 |
| Liquid paraffin | 5 |
| Squalane | 3 |
| Macadamia nut oil | 2 |
| Polysorbate 60 | 1.5 |
| Sorbitan sesquioleate | 0.5 |
| Carboxyvinyl polymer | 1 |
| Preservative, pigment | adequate amount |
| Fragrance | adequate amount |
| Purified water | remaining amount |
| Sum | 100 |

Formulation Example 4. Essence

An essence comprising the compound of the present invention prepared in Example <1-2> above and consisting of the composition below was prepared according to the general method for preparing essences.

TABLE 9

| Ingredient | Content (wt %) |
|---|---|
| Compound of the present invention | 2.5 |
| Glycerine | 10 |
| 1,3-Butylene glycol | 5 |
| PEG 1500 | 2 |
| Allantoin | 0.1 |
| DL-Panthenol | 0.3 |
| EDTA-2Na | 0.02 |
| Hydroxyethyl cellulose | 0.1 |
| Sodium hyaluronate | 8 |
| Carboxyvinyl polymer | 0.2 |
| Triethanolamine | 0.18 |
| Octyldodeceth-16 | 0.4 |
| Ethanol | 6 |
| Fragrance, preservative, pigment | adequate amount |
| Purified water | remaining amount |
| Sum | 100 |

INDUSTRIAL AVAILABILITY

The compound having a structure in which isotretinoin and a peptide are linked to each other via a covalent bond according to the present invention exhibits excellent physiological activities such as antibiotic, anti-inflammatory, or anti-oxidative actions, as well as having outstanding properties, such as solubility in water, and the like, and thus can be applied to various industrial fields such as medicines or cosmetics.

```
[Sequence List Text]
SEQ ID NO: 1:
Arg Arg Leu Ile Asp Arg Thr Asn Ala Asn

Phe Leu Val Met

SEQ ID NO: 2:
tcggtggaca agaacagcaa

SEQ ID NO: 3:
ccttgaccaa ggagctctca

SEQ ID NO: 4:
ttcgctgatg cactgcctat

SEQ ID NO: 5:
acagactcgg cactcaatgg

SEQ ID NO: 6:
gaccgacatc gaaggtgaag

SEQ ID NO: 7:
aagagaggag ctcaatgtgg c

SEQ ID NO: 8:
ggagccaaaa gggtcatcat

SEQ ID NO: 9:
gtgatggcat ggactgtggt

SEQ ID NO: 10:
gaatgtttgg ggatatttca g

SEQ ID NO: 11:
ttctgctatc agtctgtcca g

SEQ ID NO: 12:
catcagcgta aatggggatt

SEQ ID NO: 13:
acacattcca ccaccagctt
```

-continued

SEQ ID NO: 14:
gaggtcaaca acccacaggt

SEQ ID NO: 15:
gggacaatct cttccccacc

SEQ ID NO: 16:
ttcgacacat gggataacga

SEQ ID NO: 17:
tctttcaaca cgcaggacag

SEQ ID NO: 18:
aaagaggcac tgccagaaaa

SEQ ID NO: 19:
atctgaggtg cccatgctac

SEQ ID NO: 20:
ggtcaacctc aaagtcttta actc

SEQ ID NO: 21:
ttaaaaatgc aagtaagttt gctg

SEQ ID NO: 22:
aacatccaac cttcccaaac g

SEQ ID NO: 23:
gaccctaagc ccccaattct c

SEQ ID NO: 24:
cgtaccaagt agccaaggca

SEQ ID NO: 25:
caggaacgca cagtctcagt

SEQ ID NO: 26:
ccgccgagag atcgagaac

SEQ ID NO: 27:
cagttgcctg gtgaagcaag

SEQ ID NO: 28:
ggacacacac acacctg

SEQ ID NO: 29:
ccctttcgca gcaactttag

SEQ ID NO: 30:
tcgtggatgt tggtggagct

SEQ ID NO: 31:
tgtggcctca ttcctccta

---

The invention claimed is:

1. An anti-oxidative composition comprising a compound, wherein the compound having a structure in which isotretinoin and a peptide are linked to each other via a covalent bond; wherein the peptide is a peptide having the amino acid sequence consisting of SEQ ID NO: 1.

2. The anti-oxidative composition of claim 1, wherein the composition is in the form of a cosmetic composition.

3. The anti-oxidative composition of claim 2, wherein the cosmetic composition has the formulation selected from the group consisting of a skin softener, a nutrition lotion, a nutrition cream, a massage cream, an essence, an eye cream, a cleansing cream, a cleansing foam, a cleansing water, a pack, a spray, a powder, a hair tonic, a hair cream, a hair lotion, a hair shampoo, a hair rinse, a hair conditioner, a hair spray, a hair aerosol, a pomade, a sol-gel, an emulsion, an oil, a wax, and an aerosol.

* * * * *

SEQUENCE LISTING

<160> NUMBER OF SEQ ID NOS: 31

<210> SEQ ID NO 1
<211> LENGTH: 14
<212> TYPE: PRT
<213> ORGANISM: Artificial Sequence
<220> FEATURE:
<223> OTHER INFORMATION: Peptide 1

<400> SEQUENCE: 1

Arg Arg Leu Ile Asp Arg Thr Asn Ala Asn Phe Leu Val Met
1               5                   10

<210> SEQ ID NO 2
<211> LENGTH: 20
<212> TYPE: DNA
<213> ORGANISM: Artificial Sequence
<220> FEATURE:
<223> OTHER INFORMATION: Forward primer for cEBP-alpha

<400> SEQUENCE: 2
tcggtggaca agaacagcaa                                                  20

<210> SEQ ID NO 3
<211> LENGTH: 20
<212> TYPE: DNA
<213> ORGANISM: Artificial Sequence
<220> FEATURE:
<223> OTHER INFORMATION: Reverse primer for cEBP-alpha

<400> SEQUENCE: 3
ccttgaccaa ggagctctca                                                  20

<210> SEQ ID NO 4
<211> LENGTH: 20
<212> TYPE: DNA
<213> ORGANISM: Artificial Sequence
<220> FEATURE:
<223> OTHER INFORMATION: Forward primer for PPAR-gamma

<400> SEQUENCE: 4
ttcgctgatg cactgcctat                                              20

<210> SEQ ID NO 5
<211> LENGTH: 20
<212> TYPE: DNA
<213> ORGANISM: Artificial Sequence
<220> FEATURE:
<223> OTHER INFORMATION: Reverse primer for PPAR-gamma

<400> SEQUENCE: 5
acagactcgg cactcaatgg                                              20

<210> SEQ ID NO 6
<211> LENGTH: 20
<212> TYPE: DNA
<213> ORGANISM: Artificial Sequence
<220> FEATURE:
<223> OTHER INFORMATION: Forward primer for SREBP1c

<400> SEQUENCE: 6
gaccgacatc gaaggtgaag                                              20

<210> SEQ ID NO 7
<211> LENGTH: 21
<212> TYPE: DNA
<213> ORGANISM: Artificial Sequence
<220> FEATURE:
<223> OTHER INFORMATION: Reverse primer for SREBP1c

<400> SEQUENCE: 7
aagagaggag ctcaatgtgg c                                            21

<210> SEQ ID NO 8
<211> LENGTH: 20
<212> TYPE: DNA
<213> ORGANISM: Artificial Sequence
<220> FEATURE:
<223> OTHER INFORMATION: Forward primer for GAPDH

<400> SEQUENCE: 8
ggagccaaaa gggtcatcat                                              20

<210> SEQ ID NO 9
<211> LENGTH: 20
<212> TYPE: DNA
<213> ORGANISM: Artificial Sequence
<220> FEATURE:
<223> OTHER INFORMATION: Reverse primer for GAPDH

<400> SEQUENCE: 9
gtgatggcat ggactgtggt                                              20

<210> SEQ ID NO 10
<211> LENGTH: 21
<212> TYPE: DNA
<213> ORGANISM: Artificial Sequence
<220> FEATURE:
<223> OTHER INFORMATION: Forward primer for ACC

<400> SEQUENCE: 10
gaatgtttgg ggatatttca g                                            21

<210> SEQ ID NO 11
<211> LENGTH: 21
<212> TYPE: DNA

<213> ORGANISM: Artificial Sequence
<220> FEATURE:
<223> OTHER INFORMATION: Reverse primer for ACC

<400> SEQUENCE: 11
ttctgctatc agtctgtcca g                                    21

<210> SEQ ID NO 12
<211> LENGTH: 20
<212> TYPE: DNA
<213> ORGANISM: Artificial Sequence
<220> FEATURE:
<223> OTHER INFORMATION: Forward primer for aP2

<400> SEQUENCE: 12
catcagcgta aatgggatt                                       20

<210> SEQ ID NO 13
<211> LENGTH: 20
<212> TYPE: DNA
<213> ORGANISM: Artificial Sequence
<220> FEATURE:
<223> OTHER INFORMATION: Reverse primer for aP2

<400> SEQUENCE: 13
acacattcca ccaccagctt                                      20

<210> SEQ ID NO 14
<211> LENGTH: 20
<212> TYPE: DNA
<213> ORGANISM: Artificial Sequence
<220> FEATURE:
<223> OTHER INFORMATION: Forward primer for IFN-gamma

<400> SEQUENCE: 14
gaggtcaaca acccacaggt                                      20

<210> SEQ ID NO 15
<211> LENGTH: 20
<212> TYPE: DNA
<213> ORGANISM: Artificial Sequence
<220> FEATURE:
<223> OTHER INFORMATION: Reverse primer for IFN-gamma

<400> SEQUENCE: 15
gggacaatct cttccccacc                                      20

<210> SEQ ID NO 16
<211> LENGTH: 20
<212> TYPE: DNA
<213> ORGANISM: Artificial Sequence
<220> FEATURE:
<223> OTHER INFORMATION: Forward primer for IL-1beta

<400> SEQUENCE: 16
ttcgacacat gggataacga                                      20

<210> SEQ ID NO 17
<211> LENGTH: 20
<212> TYPE: DNA
<213> ORGANISM: Artificial Sequence
<220> FEATURE:
<223> OTHER INFORMATION: Reverse primer for IL-1beta

<400> SEQUENCE: 17
tctttcaaca cgcaggacag                                      20

```
<210> SEQ ID NO 18
<211> LENGTH: 20
<212> TYPE: DNA
<213> ORGANISM: Artificial Sequence
<220> FEATURE:
<223> OTHER INFORMATION: Forward primer for IL-6

<400> SEQUENCE: 18
aaagaggcac tgccagaaaa                                              20

<210> SEQ ID NO 19
<211> LENGTH: 20
<212> TYPE: DNA
<213> ORGANISM: Artificial Sequence
<220> FEATURE:
<223> OTHER INFORMATION: Reverse primer for IL-6

<400> SEQUENCE: 19
atctgaggtg cccatgctac                                              20

<210> SEQ ID NO 20
<211> LENGTH: 24
<212> TYPE: DNA
<213> ORGANISM: Artificial Sequence
<220> FEATURE:
<223> OTHER INFORMATION: Forward primer for IL-17A

<400> SEQUENCE: 20
ggtcaacctc aaagtcttta actc                                         24

<210> SEQ ID NO 21
<211> LENGTH: 24
<212> TYPE: DNA
<213> ORGANISM: Artificial Sequence
<220> FEATURE:
<223> OTHER INFORMATION: Reverse primer for IL-17A

<400> SEQUENCE: 21
ttaaaaatgc aagtaagttt gctg                                         24

<210> SEQ ID NO 22
<211> LENGTH: 21
<212> TYPE: DNA
<213> ORGANISM: Artificial Sequence
<220> FEATURE:
<223> OTHER INFORMATION: Forward primer for TNF-alpha

<400> SEQUENCE: 22
aacatccaac cttcccaaac g                                            21

<210> SEQ ID NO 23
<211> LENGTH: 21
<212> TYPE: DNA
<213> ORGANISM: Artificial Sequence
<220> FEATURE:
<223> OTHER INFORMATION: Reverse primer for TNF-alpha

<400> SEQUENCE: 23
gaccctaagc ccccaattct c                                            21

<210> SEQ ID NO 24
<211> LENGTH: 20
<212> TYPE: DNA
<213> ORGANISM: Artificial Sequence
<220> FEATURE:
```

<223> OTHER INFORMATION: Forward primer for CPT1a

<400> SEQUENCE: 24
cgtaccaagt agccaaggca                          20

<210> SEQ ID NO 25
<211> LENGTH: 20
<212> TYPE: DNA
<213> ORGANISM: Artificial Sequence
<220> FEATURE:
<223> OTHER INFORMATION: Reverse primer for CPT1a

<400> SEQUENCE: 25
caggaacgca cagtctcagt                          20

<210> SEQ ID NO 26
<211> LENGTH: 19
<212> TYPE: DNA
<213> ORGANISM: Artificial Sequence
<220> FEATURE:
<223> OTHER INFORMATION: Forward primer for Acox

<400> SEQUENCE: 26
ccgccgagag atcgagaac                           19

<210> SEQ ID NO 27
<211> LENGTH: 20
<212> TYPE: DNA
<213> ORGANISM: Artificial Sequence
<220> FEATURE:
<223> OTHER INFORMATION: Reverse primer for Acox

<400> SEQUENCE: 27
cagttgcctg gtgaagcaag                          20

<210> SEQ ID NO 28
<211> LENGTH: 17
<212> TYPE: DNA
<213> ORGANISM: Artificial Sequence
<220> FEATURE:
<223> OTHER INFORMATION: Forward primer for HSL

<400> SEQUENCE: 28
ggacacacac acacctg                             17

<210> SEQ ID NO 29
<211> LENGTH: 20
<212> TYPE: DNA
<213> ORGANISM: Artificial Sequence
<220> FEATURE:
<223> OTHER INFORMATION: Reverse primer for HSL

<400> SEQUENCE: 29
ccctttcgca gcaactttag                          20

<210> SEQ ID NO 30
<211> LENGTH: 20
<212> TYPE: DNA
<213> ORGANISM: Artificial Sequence
<220> FEATURE:
<223> OTHER INFORMATION: Forward primer for ATGL

<400> SEQUENCE: 30
tcgtggatgt tggtggagct                          20

```
<210> SEQ ID NO 31
<211> LENGTH: 19
<212> TYPE: DNA
<213> ORGANISM: Artificial Sequence
<220> FEATURE:
<223> OTHER INFORMATION: Reverse primer for ATGL

<400> SEQUENCE: 31
tgtggcctca ttcctccta                                              19
```